US00PP08538P

United States Patent [19]

Guillen

[11] Patent Number: Plant 8,538

[45] Date of Patent: Jan. 11, 1994

[54] GUINEA IMPATIENS NAMED BSR-202 BLUSH WHITE

[75] Inventor: Mario Guillen, Cartago, Costa Rica

[73] Assignee: George J. Ball, Inc., West Chicago, Ill.

[21] Appl. No.: 917,272

[22] Filed: Jul. 23, 1992

[51] Int. Cl.[5] ..... A01H 5/00

[52] U.S. Cl. ..... Plt./87.6

[58] Field of Search ..... Plt. 87.6

*Primary Examiner*—James R. Feyrer

*Attorney, Agent, or Firm*—Burns, Doane, Swecker & Mathis

[57] ABSTRACT

A new and distinct New Guinea Impatiens cultivar named BSR-202 Blush White is provided. This new cultivar was the result of a controlled breeding program wherein the Samia cultivar (U.S. Plant Pat. No. 6,730) was pollinated by the Equinox cultivar (U.S. Plant Pat. No. 6,297). The new cultivar forms attractive very light pink or blush white blossoms combined with a strong basal branching character and a compact small mounded growth habit and can be readily distinguished from the Equinox cultivar.

1 Drawing Sheet

SUMMARY OF THE INVENTION

The present invention comprises a new and distinctive Impatiens plant, botanically known as New Guinea Impatiens, and hereafter referred to by the cultivar name BSR-202 Blush White.

The new cultivar is the product of a planned breeding program. More specifically, the breeding program which resulted in the production of the new cultivar was carried out in a controlled environment during 1988 at Linda Vista, Cartago, Costa Rica. The female parent (i.e., the seed parent) was the Samia cultivar (U.S. Plant Pat. No. 6,730) which exhibits blush pink blossoms with dark green foliage. The male parent (i.e., the pollen parent) was the Equinox cultivar (U.S. Plant Pat. No. 6,297) which exhibits blush white blossoms with dark bronze foliage. The parentage of the new cultivar can be summarized as follows:

Samia × Equinox.

The seeds resulting from the above pollination were sown and plantlets were obtained which were physically and biologically different from each other. Selective study resulted in the identification of a single plant of the new cultivar. This plant had light pink blossoms and initially was designated BSR-202.

It was found that the cultivar of the present invention:

(a) exhibits attractive very light pink blossoms which commonly measure approximately 5.5 cm. in diameter and approximately 5.0 cm. in length,
(b) exhibits a very basal branching character, and
(c) exhibits a compact small mounded growth habit.

Asexual reproduction of the new cultivar by terminal or stem cuttings taken during February, 1990 at Santa Maria, Calif., U.S.A., has demonstrated that the characteristics of the new cultivar as herein described are firmly fixed and are retained through successive generations of such asexual propagation.

The BSR-202 Blush White cultivar has not been observed under all possible environmental conditions to date. Accordingly, it is possible that the phenotype may vary somewhat with variations in the environment, such as temperature, light intensity, and day length.

When the new cultivar of the present invention is compared to the Equinox cultivar (U.S. Plant Pat. No. 6,297), it is found that the new cultivar is more dwarf and exhibits a more vigorous mounded growth habit. The leaves of the new cultivar tend to be smaller than those of the Equinox cultivar.

When plant material of the BSR-202 Blush White cultivar is subjected to standard random amplified polymorphic DNA marker analysis (RAPD) using polymerase chain reaction (PCR) and a known unique set of DNA primers, it is found to exhibit a different fingerprint map when compared to that of the Equinox cultivar which confirms its genetic distinctiveness.

Plants of the new cultivar will be marketed under the Celebration trademark by George J. Ball, Inc.

BRIEF DESCRIPTION OF THE PHOTOGRAPH

The accompanying photograph shows as nearly true as it is reasonably possible to make the same in a color illustration of this character, a typical specimen of an overall plant of the new cultivar. The plant was grown in a greenhouse at Arroyo Grande, Calif., U.S.A.

DETAILED DESCRIPTION

The chart used in the identification of colors described herein is the R.H.S. Colour Chart of The Royal Horticultural Society, London, England. The color values were determined during the first week of January, 1992. The plants were produced from cuttings taken from stock plants and were grown at Arroyo Grande, Calif., U.S.A., under standard greenhouse conditions comparable to those used in commercial practice while utilizing a soilless growth medium and maintaining temperatures of approximately 72° F. during the day and approximately 65° F. during the night.

Propagation:

*Type cutting.*—Terminal tip.

*Time to initiate roots.*—Approximately 14 to 21 days with the shorter times generally being experienced in the summer and the longer times in the winter.

*Rooting habit.*—Fibrous and branching.

Plant description:

*Form.*—Strong basal branching.

*Habit of growth.*—Compact and small mounded. A mature plant commonly measures approximately 12 inches in height and approximately 15 inches in width.

*Foliage.*—The configuration is narrow and lanceolate. The leaves of the BSR-202 Blush White cultivar measure approxiamtely 8.0 cm.×3.0 cm. while those of the Equinox cultivar measure approximately 11.0 cm.×3.5 cm. The foliage of the BSR-202 Blush White cultivar is Green Group 139A (abaxial) and Green Group 138B (adaxial). This can be compared to Green Group 135A (abaxial) and Red-Purple Group 60A (adaxial) for the Equinox cultivar. The stem color is Green Group 134C while that of the Equinox cultivar is Greyed-Purple Group 183C. The adaxial veins and the leaf petioles are Red Group 47A. This can be compared to Greyed-Purple Group 183B for the Equinox cultivar.

Flower description:

*Flowering habit.*—Freely flowering.

*Natural flowering season.*—Year-round in greenhouse environment.

*Flowers borne.*—Above foliage, arising from leaf axils.

*Flower color.*—Very light pink or blush white, Red-Purple Group 62D (abaxial and adaxial). This can be compared to Red-Purple Group 73D (abaxial and adaxial) for the Equinox cultivar. The flower does fade somewhat to a lighter shade of the same color tone when under full sunlight, and commonly assumes a very pale pink background color of Red Group 56D. The petals commonly possess pigmented attachment points and veins that approximate Red-Purple Group 60C and lighter. Such coloration contributes to the blushed appearance.

*Quantity of flowers.*—Approximately 5 to 10 per stem.

*Number of petals.*—Five.

*Flower diameter.*—Approximately 5.5 cm. which can be compared to approximately 5.5 cm. for the Equinox cultivar.

*Nectary length.*—Approximately 4.5 cm. which can be compared to approximately 6.0 cm. for the Equinox cultivar.

*Nectary color.*—Green Group 134C which can be compared to Greyed-Red Group 182A for the Equinox cultivar.

*Reproductive organs.*—The anthers are fused together forming one organ that surrounds the pistil. Generally, the anters shed pollen prior to the stigma becoming receptive. The pollen color is cream-white, White Group 155D. The stigma color is Red-Purple Group 62A and can be compared to Red-Purple Group 57B exhibited by the Equinox cultivar. The ovary color is Yellow-Green Group 144A and can be compared to Yellow-Green Group 144A exhibited by the Equinox cultivar.

I claim:

1. A new and distinct cultivar of New Guinea Impatiens named BSR-202 Blush White, substantially as herein shown and described, which:

(a) exhibits attractive very light pink blossoms which commonly measure approximately 5.5 cm. in diameter and approximately 5.0 cm. in length,
(b) exhibits a very basal branching character, and
(c) exhibits a compact small mounded growth habit.

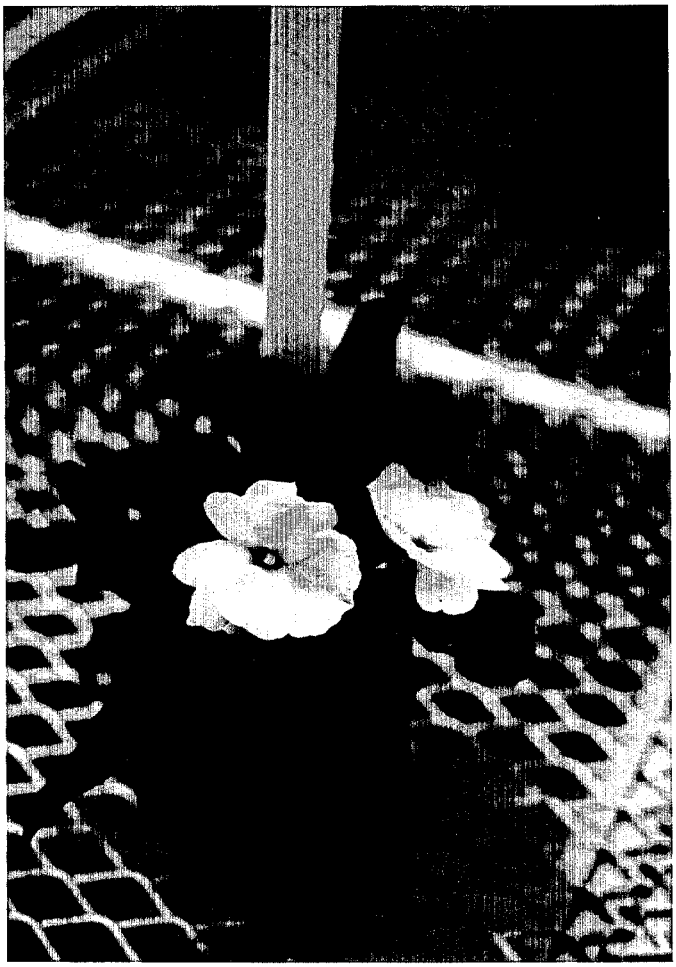

* * * * *